(12) United States Patent
Ishihara et al.

(10) Patent No.: US 8,375,688 B2
(45) Date of Patent: Feb. 19, 2013

(54) PACKAGE OF FREEZE STORAGE CONTAINER AND PROCESS FOR PRODUCING THE SAME

(75) Inventors: Kazuki Ishihara, Osaka (JP); Hideaki Murahashi, Osaka (JP); Naomi Nakatani, Osaka (JP); Yoshihiro Yoshikawa, Osaka (JP); Akio Shirasu, Osaka (JP); Hidenori Ozaki, Settsu (JP)

(73) Assignees: Nipro Corporation, Osaka (JP); Daikin Industries, Ltd., Osaka (JP)

( * ) Notice: Subject to any disclaimer, the term of this patent is extended or adjusted under 35 U.S.C. 154(b) by 0 days.

(21) Appl. No.: 13/167,611

(22) Filed: Jun. 23, 2011

(65) Prior Publication Data

US 2011/0252748 A1    Oct. 20, 2011

Related U.S. Application Data

(62) Division of application No. 11/887,073, filed as application No. PCT/JP2006/306188 on Mar. 27, 2006, now abandoned.

(30) Foreign Application Priority Data

Mar. 25, 2005  (JP) .................................. 2005-090011
Apr. 26, 2005  (JP) .................................. 2005-128458

(51) Int. Cl.
*B65B 11/00* (2006.01)

(52) U.S. Cl. .............................. 53/461; 53/463; 493/267
(58) Field of Classification Search ................... 53/461, 53/463; 493/267
See application file for complete search history.

(56) References Cited

U.S. PATENT DOCUMENTS

| | | | |
|---|---|---|---|
| 3,942,529 A | 3/1976 | Waage | |
| 4,112,989 A | 9/1978 | Grode et al. | |
| 5,209,745 A | 5/1993 | Irr et al. | |
| 5,253,754 A | 10/1993 | Soodak | |
| 6,392,138 B1 | 5/2002 | Ichiba et al. | |

FOREIGN PATENT DOCUMENTS

| | | |
|---|---|---|
| DE | 1611928 A1 | 2/1971 |
| EP | 0976544 A1 | 2/2000 |
| GB | 1162461 | 8/1969 |
| JP | 49-8079 | 2/1974 |
| JP | 54-144275 A | 11/1979 |
| JP | 55-044977 B2 | 11/1980 |
| JP | 55-55069 Y2 | 12/1980 |
| JP | 62-057351 B2 | 11/1987 |
| JP | 6-263951 A | 9/1994 |
| JP | 6-271733 A | 9/1994 |
| JP | 8-173505 A | 7/1996 |
| JP | 11-139459 A | 5/1999 |
| JP | 2003-267471 A | 9/2003 |
| KR | 10-2001-0006032 A | 1/2001 |
| WO | 9846426 A1 | 10/1998 |
| WO | 0020489 A1 | 4/2000 |
| WO | 2004018201 A1 | 3/2004 |

*Primary Examiner* — Thanh Truong
(74) *Attorney, Agent, or Firm* — Sughrue Mion, PLLC

(57) ABSTRACT

A package for a cryopreservation container including at least an adhesive fluoropolymer film. The package for a cryopreservation container makes it possible to store blood, rare cells and vital tissues in a very low temperature environment without any damage to the container. Further, the sealing strength resulting from heat sealing after placing a cryopreservation container in the packages is very good. Therefore, liquid nitrogen can be inhibited from entering the inside and thus contamination with bacteria, viruses or the like contained in liquid nitrogen can be avoided and the package can be prevented from being broken by expansion of intruder liquid nitrogen on the occasion of thawing. Also disclosed is a method for packaging a cryopreservation container and a method of producing a package for a cryopreservation container.

9 Claims, No Drawings

PACKAGE OF FREEZE STORAGE CONTAINER AND PROCESS FOR PRODUCING THE SAME

CROSS-REFERENCE TO RELATED APPLICATIONS

This is a Rule 53(b) Divisional of application Ser. No. 11/887,073 filed Sep. 25, 2007, which is a 371 of PCT Application No. PCT/JP2006/306188 filed Mar. 27, 2006, which claims benefit of Japanese Patent Application No. 2005-090011 filed Mar. 25, 2005 and Japanese Patent Application No. 2005-128458 filed Apr. 26, 2005. The above-noted applications are incorporated herein by reference in their entirety.

TECHNICAL FIELD

The present invention relates to a package for a cryopreservation container and a method of producing the same. More particularly, it relates to a package for a cryopreservation container which comprises a laminate film and is used for packaging a cryopreservation container and in which the laminated film comprises a low-temperature resistant resin film and an adhesive fluoropolymer film, with the adhesive fluoropolymer film being disposed at least on one outermost layer.

BACKGROUND ART

Blood, rare cells and vital tissues are generally stored at very low temperatures, namely at about −80 to −196° C. In particular, bone marrow cells, hematopoietic stem cells and like rare cells are effectively used in the treatment of intractable diseases such as leukemia, and a technology of storing them for a long period of time has been demanded. For the storage at such very low temperatures, blood, rare cells and vital tissues are generally stored in tightly closed containers therefor immersed mainly in liquid nitrogen.

As for the cryopreservation containers for such storage, vials made of polypropylene, for instance, are commercially available for use on the laboratory level; they are inexpensive and convenient from the handling viewpoint.

With the recent development of cord blood banks, bag-like containers excellent in low-temperature resistance and flexibility have been proposed. For example, containers made of a laminated film composed of a polyimide film and fluorinated ethylene-propylene polymer film (Patent Document 1) and containers made of a tetrafluoroethylene-ethylene copolymer film (Patent Document 2) have been proposed. Further, Patent Document 3 discloses cryopreservation containers molded from an electron beam-irradiated, biaxially stretched ethylene-vinyl acetate copolymer film. Patent Document 4 discloses cryopreservation containers molded from a biaxially stretched, crosslinked polyethylene film.

On the other hand, the present inventors developed cryopreservation containers which are constituted of a laminated film consisting of an ultrahigh molecular weight polyethylene layer and a thermoplastic resin layer compatible with the ultrahigh molecular weight polyethylene layer and are superior to the cryopreservation containers disclosed in Patent Documents 1 to 4, and applied for a patent for the same (Patent Document 5).

When blood, rare cells and vital tissues are preserved in the cryopreservation containers mentioned above in liquid nitrogen, the cryopreservation containers are further packaged so that the contents may be protected in case of damage of the containers and liquid nitrogen may be prevented from entering the cryopreservation containers. For packaging them, packages made of a perfluoroethylene-propene copolymer, among others, are generally used.

However, such packages are fluororesin-made ones and therefore the molding or processing for manufacturing them must be carried out at elevated temperatures. In spite of this, their heat seal strength is not so high but the sealed portions are possibly in danger of peeling away. After packaging of a cryopreservation container in a package, the mouth portion of the package is heat sealed for tight closure. This mouth portion is also susceptible to peeling and there is the possibility that liquid nitrogen may enter the inside. This work is carried out in medical institutions such as cord blood banks and heat sealing under severe conditions is a burden on workers. Further, when polypropylene vials for cryopreservation or cryopreservation containers described in Patent Documents 1 to 4 are packaged, there is the possibility that when the packages are damaged and liquid nitrogen enters the inside, the cryopreservation containers may also be damaged.

Ultrahigh molecular weight polyethylene films are formed by cutting processing and are relatively thick. When they are used as materials for packages, the conduction of heat to the contents may possibly be affected.

Known as materials for packages for cryopreservation containers are polytetrafluoroethylene, polychlorotrifluoroethylene, tetrafluoroethylene/hexafluoropropylene copolymers, tetrafluoroethylene/ethylene copolymers and polyimides, among others (cf. e.g. Patent Document 6 and Patent Document 7). However, those fluororesins which are used in preparing the conventional packages require elevated temperatures for sealing and their sealability is insufficient in some cases.

Patent Document 1: Japanese Patent Publication S49-008079
Patent Document 2: Utility Model Publication S55-055069
Patent Document 3: Japanese Patent Publication S55-044977
Patent Document 4: Japanese Patent Publication S62-057351
Patent Document 5: Japanese Kokai Publication H08-173505
Patent Document 6: Japanese Kokai Publication H11-139459
Patent Document 7: Japanese Kokai Publication 2003-267471

DISCLOSURE OF INVENTION

Problems which the Invention is to Solve

Therefore, it is demanded that packages for cryopreservation containers which can prevent the conventional cryopreservation containers stored at very low temperatures, namely −80 to −196° C., from being damaged and are excellent in heat sealability be developed.

Means for Solving the Problems

The present inventors proposed using an adhesive fluoropolymer film for a package for a cryopreservation container.

The present invention relates to:
(1) a package for a cryopreservation container comprising at least an adhesive fluoropolymer film;
(2) the package for a cryopreservation container according to (1), wherein the adhesive fluoropolymer film is made of an adhesive fluoropolymer containing at least one adhesive site;
(3) the package for a cryopreservation container according to (2), wherein the at least one adhesive site is selected from the group consisting of carbon-carbon double bond, carbonyl group [—C(=O)], carbonyl group-containing groups or bonds, hydroxyl group, cyano group, sulfonic acid group and epoxy group;

(4) the package for a cryopreservation container according to (3), wherein the adhesive fluoropolymer contains at least one reactive functional group as the adhesive site and is a copolymer obtained by copolymerizing the following monomers (A) and (B):

(A) a fluorinated monomer containing no reactive functional group;

(B) a fluorinated monomer containing the at least one reactive functional group.

(5) the package for a cryopreservation container according to (4), wherein the fluorinated monomer containing no reactive functional group is represented by the formula (1) given below:

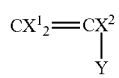

(wherein $X^1$ and $X^2$ each is hydrogen atom or halogen atom and Y is hydrogen atom, fluorine atom, a fluorinated alkyl group containing 1 to 5 carbon atoms or a fluorinated oxyalkyl group containing 1 to 5 carbon atoms);

(6) the package for a cryopreservation container according to (5), wherein the fluorinated monomer containing no reactive functional group comprises at least one monomer selected from the group consisting of tetrafluoroethylene, vinylidene fluoride, 1,2-difluorochloroethylene, hexafluoropropylene, perfluoro(vinyl methyl ether) and perfluoro(vinyl propyl ether);

(7) the package for a cryopreservation container according to (4) to (6), wherein the fluorinated monomer containing the at least one reactive functional group is represented by the formula (2) given below:

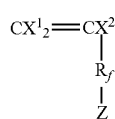

(wherein $X^1$ and $X^2$ each is hydrogen atom or halogen atom, Z is hydroxyl group, carboxyl group, cyano group, sulfonic acid group or epoxy group and $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond);

(8) the package for a cryopreservation container according to (4), wherein the adhesive fluoropolymer is represented by the formula (3) given below:

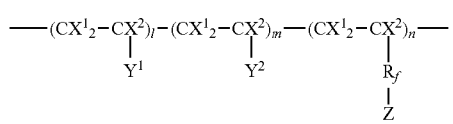

(wherein $X^1$ and $X^2$ each is hydrogen atom or halogen atom, $Y^1$ and $Y^2$ each is hydrogen atom, fluorine atom, a fluorinated alkyl group containing 1 to 5 carbon atoms or a fluorinated alkoxy group containing 1 to 5 carbon atoms, Z is hydroxyl group, carboxyl group, cyano group, sulfonic acid group or epoxy group, $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond and the ratio (l+m)/n is 2 to 2000);

(9) the package for a cryopreservation container according to (3), wherein the adhesive fluoropolymer comprises a fluorinated monomer-derived fluorinated monomer unit and a nonfluorinated monomer-derived nonfluorinated monomer unit;

(10) the package for a cryopreservation container according to claim 9, wherein the fluorinated monomer is tetrafluoroethylene and the nonfluorinated monomer is ethylene;

(11) the package for a cryopreservation container according to claim 1 comprising the adhesive fluoropolymer film on at least one outermost layer and a film other than the adhesive fluoropolymer film;

(12) the package for a cryopreservation container according to (11), wherein the film other than the adhesive fluoropolymer film is a low-temperature resistant resin film;

(13) the package for a cryopreservation container according to (12), wherein the low-temperature resistant resin comprises at least one resin selected from the group consisting of ultrahigh molecular weight polyethylene, polyimides, polytetrafluoroethylene, ethylene-tetrafluoroethylene copolymers and ethylene-vinyl acetate copolymers;

(14) the package for a cryopreservation container according to (13), wherein the low-temperature resistant resin is a polyimide;

(15) a method of producing a package for a cryopreservation container comprising shaping an adhesive fluoropolymer film into a bag-like article by heat sealing; and

(16) the method of producing a package for a cryopreservation container according to (15), comprising shaping a laminated film comprising the adhesive fluoropolymer film on at least one outermost layer and a film other than the adhesive fluoropolymer film, into a bag-like article by heat sealing.

Effects of the Invention

The package for a cryopreservation container according to the invention makes it possible to store blood, rare cells and vital tissues in a very low temperature environment without any damage to the container. In particular, even when it is used in combination with those cryopreservation containers (e.g. cryopreservation containers described in Patent Documents 1 to 4) which cannot always be said to be excellent in cryopreservation or polypropylene vials in use on the experiment level, the package can produce its effects. Since it is excellent in low-temperature heat sealability, the production stability in package manufacture in a factory is improved and workers at working places where biological samples are stored can seal it with ease. Further, the sealing strength resulting from heat sealing after placing a cryopreservation container in the packages is very good and, therefore, liquid nitrogen can be inhibited from entering the inside and thus contamination with bacteria, viruses or the like contained in liquid nitrogen can be avoided and the package can be prevented from being broken by expansion of intruder liquid nitrogen on the occasion of thawing.

BEST MODES FOR CARRYING OUT THE INVENTION

The package for a cryopreservation container according to the invention is a bag-shaped package for packaging the cryopreservation container for the purpose of protecting the contents of the cryopreservation container in case of the same being damaged and for the purpose of preventing liquid nitrogen from entering the cryopreservation container and is constituted of a film comprising at least an adhesive fluoropolymer layer.

The adhesive fluoropolymer film is a film molded from a polymer whose main chain and/or side chains contain at least one fluorine atom and that film functions as a film adhering to a substrate or base made of an organic material. The adhesion or adhering, so referred to herein, is the binding of the adhesive fluoropolymer film to the organic material via physical and/or chemical bonds, among others. From the bond strength viewpoint, chemical bonds are preferred although the bonds are not limited thereto. The chemical bonds include covalent bonds, ionic bonds, coordination bonds, hydrogen bonds and intermolecular forces, among others. Preferred bonds from the bond strength viewpoint are, but are not limited to, covalent bonds and ionic bonds. More preferred are covalent bonds.

The organic material mentioned above includes general-purpose resin moldings, such as films, tubes, synthetic fibers, synthetic rubbers and solids, made of polyethylene, polycarbonates, polystyrene, polyvinyl chloride, polyvinyl acetate, polyesters and low-temperature-resistant resins such as ultrahigh molecular weight polyethylene, polyimides, polytetrafluoroethylene, ethylene-tetrafluoroethylene copolymers and ethylene-vinyl acetate copolymers, and naturally occurring organic matters such as natural rubbers, natural fibers, woods, papers and leathers and, further, adhesive fluoropolymers. Preferred ones among these from the viewpoint of improving the low-temperature resistance of the package itself are, but are not limited to, the adhesive fluoropolymer film itself and ones having a function enabling their adhesion to the low-temperature-resistant resin film.

From the moldability/processability viewpoint, the adhesive fluoropolymer has a number average molecular weight of about 1,000 to 1,000,000, preferably about 2,000 to 500,000, more preferably about 5,000 to 300,000. These ranges have no restrictive meaning, however.

The adhesive fluoropolymer film can be produced by timely selecting a proper production method according to the molecular structure, glass transition temperature and melting point, among others, of the adhesive fluoropolymer, as the one skilled in the art does. For example, there may be mentioned compression molding, injection molding, extrusion molding, T-die molding, inflation molding, solvent casting and so forth. A method preferred from the moldability/processability viewpoint is, but is not limited to, compression molding. Considering the conduction of heat to the contents, the adhesive fluoropolymer film has a thickness of about 10 to 100 μm, preferably 10 to 50 μm, particularly preferably 10 to 30 μm. These ranges have no restrictive meaning, however.

Preferred examples of the adhesive fluoropolymer are copolymers derived from the following (A) and (B).
(A) A fluorinated monomer containing no reactive functional group.
(B) A fluorinated monomer containing at least one reactive functional group.

The reactive functional group, so referred to herein, is a functional group capable of adhering to the organic material substrate mentioned above via a covalent bond, ionic bond, coordination bond or hydrogen bond, for instance. For example, such functional group includes, but is not limited to, hydroxyl group, carboxyl group, cyano group, sulfonic acid group, epoxy group and like groups. One preferred among these is, but is not limited to, the hydroxyl group which is readily activated by heat.

The fluorinated monomer mentioned above is one giving a copolymer whose main chain and/or side chains contains at least one fluorine atom substituting for a hydrogen atom. It includes, for example, fluorinated ethylenic monomers, fluorinated ester monomers and fluorinated wholly aromatic monomers. Preferred ones are, but are not limited to, fluorinated ethylenic monomers in view of their ready availability and moldability/processability of the copolymers obtained.

The copolymer mentioned above may be a binary one derived from at least one (A) monomer and at least one (B) monomer by polymerization. For example, mention may be made of a binary one derived from one (A) monomer and one (B) monomer, a ternary one derived from two (A) monomers and one (B) monomer, and a ternary one derived from one (A) monomer and two (B) monomers. Preferred ones from the production cost viewpoint are, but are not limited to, binary or ternary ones.

As the copolymerization technique, there may be mentioned, among others, radical copolymerization, anion copolymerization, cation copolymerization, emulsion copolymerization and plasma copolymerization and an appropriate technique can be timely selected from among these according to the monomer structure, polarity, solvent species and so forth, as the one skilled in the art does. A preferred one among them is, but is not limited to, radical copolymerization in view of the ease of production.

As for the constitution of the copolymer, there may be mentioned random copolymers, block copolymers, graft copolymers and alternating copolymers. Preferred ones are, but are not limited to, random copolymers from the ease of production viewpoint.

Further, the occurrence ratio (copolymerization ratio) between and (B) in the above copolymer is, but is not limited to, 1 to 2000 of (A), preferably 100 to 2000 of (A), with (B) being taken as 1 in view of the moldability/processability of the copolymer.

The above-mentioned fluorinated monomer (A) containing no reactive functional group has none of the reactive functional groups enumerated hereinabove and gives a copolymer whose main chain and/or side chains contain at least one fluorine atom substituting for a hydrogen atom. Preferred ones are, but are not limited to, fluorinated ethylenic monomers containing no reactive functional group in view of their ready availability and of the moldability/processability of the copolymers obtained.

The fluorinated monomer (A) containing no reactive functional group contains at least one fluorine atom and, as examples thereof, there may be mentioned monomers represented by the following formula (1).

(1)

(In the above formula, $X^1$ and $X^2$ each is hydrogen atom or halogen atom and Y is hydrogen atom, fluorine atom, a fluorinated alkyl group containing 1 to 5 carbon atoms or a fluorinated oxyalkyl group containing 1 to 5 carbon atoms.)

As the monomers represented by the above formula (1), there may be mentioned, for example, tetrafluoroethylene, vinylidene fluoride, 1,2-difluorochloroethylene, hexafluoropropylene, perfluoro (vinyl methyl ether) and perfluoro (vinyl propyl ether). Preferred are tetrafluoroethylene, vinylidene fluoride, 1,2-difluorochloroethylene and perfluoro (vinyl propyl ether). Preferred ones are, but are not limited to, tetrafluoroethylene, vinylidene fluoride, hexafluoropropylene and perfluoro (vinyl propyl ether) in view of their ready availability and of the moldability/processability of the copolymers obtained.

On the other hand, the fluorinated monomer (B) containing at least one reactive functional group contains at least one of the reactive functional groups enumerated hereinabove, and the copolymer obtained by polymerization using the same contains at least one fluorine atom substituting for a hydrogen atom in the main chain and/or side chains thereof. Preferred ones are, but are not limited to, fluorinated ethylenic monomers containing a reactive functional group or groups in view of their ready availability and of the moldability/processability of the copolymers obtained.

As examples of the fluorinated ethylenic monomer (B) containing at least one reactive functional group, there may be mentioned monomers represented by the formula (2).

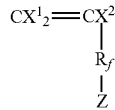
(2)

(In the above formula, $X^1$ and $X^2$ each is hydrogen atom or halogen atom, Z is hydroxyl group, carboxyl group, cyano group, sulfonic acid group or epoxy group and $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond.)

As the monomers represented by the above formula (2), there may be mentioned, for example,
perfluoro (4-oxa-5-hexenol) (formula (4)),
perfluoro (1,1-dihydro-6-heptenol) (formula (5)),
perfluoro (1,1,9,9-tetrahydro-2,5-bistrifluoromethyl-3,6-dioxa-8-nonenol) (formula (6)), perfluoro (4-oxa-5-hexenoic acid) (formula (7)),
perfluoro (3,6-dioxa-4-trifluoromethyl-7-octenonitrile) (formula (8)),
perfluoro (1,1,-dihydro-3-oxa-4-pentenesulfonic acid) (formula (9)), 1,2-epoxy-per fluoro (1,1,2-trihydro-6-pentene) (formula (10)) and like monomers. Preferred ones are, but are not limited to, hydroxyl group-containing ones such as
perfluoro (4-oxa-5-hexenol) (formula (4)),
perfluoro (1,1-dihydro-6-heptenol) (formula (5)) and
perfluoro (1,1,9,9-tetrahydro-2,5-bistrifluoromethyl-3,6-dioxa-8-nonenol) (formula (6)) in view of their giving copolymers excellent in low-temperature heat sealability.

$$CF_2=CF-OCF_2CF_2CF_2-OH \qquad (4)$$

$$CF_2=CF-CF_2CF_2CF_2CF_2CH_2-OH \qquad (5)$$

(6)

$$CF_2=CF-OCF_2CF_2CF_2-COOH \qquad (7)$$

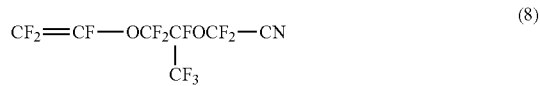
(8)

(9)

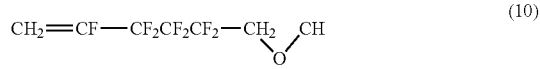
(10)

Preferred constitutions of the adhesive fluoropolymer to be used in the practice of the invention are, but are not limited to, copolymers represented by the formula (3) given below in view of the ease of production thereof.

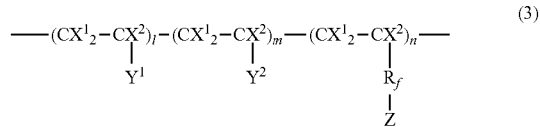
(3)

(In the above formula, $X^1$ and $X^2$ each is hydrogen atom or halogen atom, $Y^1$ and $Y^2$ each is hydrogen atom, fluorine atom, a fluorinated alkyl group containing 1 to 5 carbon atoms or a fluorinated alkoxy group containing 1 to 5 carbon atoms, Z is hydroxyl group, carboxyl group, cyano group, sulfonic acid group or epoxy group, $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond and the ratio (l+m)/n is 2 to 2000.) When the ratio (l+m)/n is in excess of 2000, there is the possibility that no sufficient adhesiveness can be obtained any longer.

More preferred constitutions of the adhesive fluoropolymer to be used in the practice of the invention are, but are not limited to, copolymers represented by the formula (11) given below in view of the ease of production thereof and from the heat seal strength viewpoint.

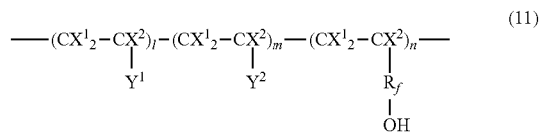
(11)

(In the above formula, $X^1$ and $X^2$ each is hydrogen atom or halogen atom, $Y^1$ and $Y^2$ each is hydrogen atom, fluorine atom, a fluorinated alkyl group containing 1 to 5 carbon atoms or a fluorinated alkoxy group containing 1 to 5 carbon atoms, $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond and the ratio (l+m)/n is 2 to 2000.)

Particularly preferred constitutions of the adhesive fluoropolymer to be used in the practice of the invention are, but are not limited to, copolymers of tetrafluoroethylene and/or perfluoro(vinyl propyl ether) and perfluoro(1,1,9,9-tetrahydro-2,5-bistrifluoromethyl-3,6-dio xa-8-nonenol) from the viewpoint of ready availability of the monomers, the ease of production and the heat seal strength. From the ease of production viewpoint, the copolymer constituent ratio is a total of about 2 to 2000, preferably about 4 to 2000, tetrafluoroethylene monomer units and/or perfluoro (vinyl propyl ether) monomer units per perfluoro (1,1,9,9-tetrahydro-2,5-bistrifluoromethyl-3,6-dia xa-8-nonenol) monomer unit. The ranges given above have no restrictive meaning, however.

In the practice of the invention, the adhesive fluororesin film mentioned above is preferably one made of an adhesive fluoropolymer containing at least one adhesive site.

The adhesive fluoropolymer may contain the above-mentioned reactive functional groups as the adhesive sites.

The adhesive fluororesin film may be one forming an adhesive fluororesin layer to be described later herein. The adhesive fluoropolymer may be one constituting an adhesive fluororesin.

In the practice of the invention, the adhesive fluororesin layer is made of the adhesive fluororesin.

The adhesive fluororesin, so referred to herein, is preferably one comprising a fluoropolymer containing at least one adhesive site.

The fluoropolymer, so referred to herein, is a polymer containing fluorinated monomer units derived from a fluorinated monomer or monomers in the main chain thereof. The fluoropolymer may or may not contain nonfluorinated monomer units derived from a nonfluorinated monomer or monomers.

The term "monomer unit" as used herein referring to the fluoropolymer, means a monomer-derived portion constituting a part of the molecular structure of the polymer. The tetrafluoroethylene unit, for instance, is represented by —(CF$_2$—CF$_2$)—.

The above-mentioned fluorinated monomer is not particularly restricted but may be any of fluorine atom-containing polymerizable compounds. Thus, for example, there may be mentioned tetrafluoroethylene [TFE], vinylidene fluoride [VdF], chlorotrifluoroethylene [CTFE], vinyl fluoride [VF], hexafluoropropylene [HFP], hexafluoroisobutene, perfluoro (alkyl vinyl ether) [PAVE] species, and monomers represented by the general formula (i):

$$CH_2=CX^3(CF_2)_nX^4 \qquad (i)$$

(wherein X$^3$ represents hydrogen atom or fluorine atom, X$^4$ represents hydrogen atom, fluorine atom or chlorine atom and n represents an integer of 1 to 10).

The above-mentioned nonfluorinated monomer is not particularly restricted but may be any of compounds containing no fluorine atom and copolymerizable with the fluorinated monomers mentioned above. For example, there may be mentioned ethylene [Et], propylene, 1-butene, 2-butene, vinyl chloride and vinylidene chloride.

As the above fluoropolymer, there may be mentioned the copolymers (I) and copolymers (II) mentioned below.
(I) Copolymers resulting from polymerization of at least TFE and Et;
(II) Copolymers resulting from polymerization of at least TFE and at least one monomer represented by the general formula (ii):

$$CF_2=CF—R_f^2 \qquad (ii)$$

(wherein R$_f^2$ represents —CF$_3$ or —OR$_f^1$ in which R$_f^1$ represents a perfluoroalkyl group containing 1 to 5 carbon atoms).

As the copolymers (I), there may be mentioned, for example, copolymers constituted of at least 20 to 80 mole percent of TFE units and 80 to 20 mole percent of Et units.

In the present specification, the mole percent values for the respective monomer units are the percentages of the numbers of moles of the respective monomers now constituting the respective monomer units in the copolymer relative to that 100 mole percent which corresponds to the total number of moles of all the monomers now constituting the monomer units constituting the molecular chain of the copolymer minus the number of moles of the monomer from which the adhesive site-containing monomer units to be mentioned later herein are derived.

The mole percent values given for the respective monomer units are the values determined from a $^{19}$F-NMR chart.

The copolymers (I) may contain, in the main chain thereof, other monomer units derived from at least one other copolymerizable monomer in addition to TFE units and Et units, and an appropriate monomer species can be selected as the other monomer according to the intended use of the laminate film to be obtained and can be subjected to copolymerization.

As the other monomer, there may be mentioned HFP, CTFE, propylene, monomers represented by the general formula (iii)

$$CX^5_2=CX^6(CF_2)_nX^7 \qquad (iii)$$

(wherein X$^5$ and X$^6$ are the same or different and each represents hydrogen atom or fluorine atom, X$^7$ represents hydrogen atom, fluorine atom or chloride atom and n represents an integer of 1 to 10), and monomers represented by the general formula (iv):

$$CF_2=CF—OR_f^1 \qquad (iv)$$

(wherein R$_f^1$ represents a perfluoroalkyl group containing 1 to 5 carbon atoms), among others. Generally, one or two of these are used.

The other monomer units may amount to 0 to 20 mole percent relative to 100 mole percent of the monomer units constituting the molecular chain of each copolymer (I).

Preferred as the above fluoropolymer are the copolymers (I) since they are excellent in thermal stability, chemical resistance, weather resistance, electric insulation properties, low liquid chemical permeability and nonstickiness, among others, and Et/TFE/HFP copolymers are more preferred since they are excellent in thermal stability, chemical resistance, weather resistance, electric insulation properties, low liquid chemical permeability, nonstickiness, low-temperature processability and transparency, among others. The HFP unit content in the Et/TFE/HFP copolymers is preferably 5 to 20 mole percent, a more preferred lower limit is 8 mole percent and a more preferred upper limit is 17 mole percent. The Et/TFE/HFP copolymers may contain, in addition to Et-, TFE- and HFP-derived units, units derived from one or more of the above-mentioned other monomer species other than HFP units within the limits within which the favorable properties of the Et/TFE/HFP copolymers will not be impaired.

In the present specification, the term "adhesive site" means a functional group showing affinity for or reactivity with the above-mentioned organic materials such as polyimide [PI] films.

In the present specification, the term "affinity" means the ability to show such an interaction with the organic materials such as PI films without modifying the chemical structure as hydrogen bonding or van der Waals force and the term "reactivity" means the ability to modify the chemical structure of the functional group, for instance.

The adhesive sites are generally possessed by the above-mentioned fluoropolymer in the main chain or side chains thereof.

The adhesive sites are not particularly restricted but include, among others, carbon-carbon double bonds, carbonyl group [—C(=O)], carbonyl group-containing groups or

bonds. In the fluoropolymer containing such an adhesive site, the adhesive sites may be of a kind or there may be two or more kinds of adhesive sites.

The above-mentioned reactive functional groups may also serve as the "adhesive sites".

As the carbonyl group-containing groups or bonds mentioned above, there may be mentioned, for example, the carbonate group, haloformyl group, formyl group, carboxyl group, carbonyloxy group [—C(=O)O—], acid anhydride group [—C(=O)O—C(=O)—], isocyanato group, amide group [—C(=O)—NH—], imide group [—C(=O)—NH—C(=O)—], urethane bond [—NH—C(=O)O—], carbamoyl group [NH$_2$—C(=O)—], carbamoyloxy group [NH$_2$—C(=O)O—], ureido group [NH$_2$—C(=O)—NH—] and oxamoyl group [NH$_2$—C(=O)—C(=O)—].

Preferred as the carbonyl group-containing groups or bonds are carbonate groups and haloformyl groups, among others, in view of the ease of introduction thereof and their high reactivity.

The above-mentioned carbonate group is a group having bonds represented by [—OC(=O)O—] and is represented by —OC(=O)O—R (in which R represents an organic group or a group IA atom, group IIA atom or group VIIB atom). As the organic group R in the above formula, there may be mentioned, for example, alkyl groups containing 1 to 20 carbon atoms and alkyl groups containing 2 to 20 carbon atoms and containing at least one oxygen atom constituting an ether bond, preferably alkyl groups containing 1 to 8 carbon atoms and alkyl groups containing 2 to 4 carbon atoms and containing an oxygen atom constituting an ether bond, among others. As the above carbonate group, there may be mentioned, for example, —OC(=O)O—CH$_3$, —OC(=O)O—C$_3$H$_7$, —OC(=O)O—C$_8$H$_{17}$ and —OC(=O)O—CH$_2$CH$_2$OCH$_2$CH$_3$.

The above-mentioned haloformyl group is represented by —COY (in which Y represents a group VIIB atom), and —COF and —COCl, among others, are preferred.

The number of the adhesive sites can be properly selected according to such factors as substrate species, shape, use and required bond strength and according to the fluoropolymer species mentioned above. Generally, it is 3 to 1000 per $1 \times 10^6$ carbon atoms in the main chain. When the number of carbonyl groups is counted, the number of the adhesive sites is generally not less than 150, preferably not less than 250, more preferably not less than 300, per $1 \times 10^6$ main chain carbon atoms.

In the present specification, the number of the above-mentioned "adhesive sites" is determined by carrying out infrared absorption spectrometry according to the method of determining the number of carbonyl group-containing functional group as described in International Publication WO 99/45044.

As the above-mentioned adhesive fluororesin, there may be mentioned, for example, those fluorine-containing ethylenic polymers containing carbonyl group-containing functional groups which are described in International Publication WO 99/45044.

The above adhesive fluororesins can be obtained by introducing adhesive sites on the occasion of fluoropolymer production by polymerization and the method of introducing adhesive sites is not particularly restricted but includes, for example, (1) the method comprising subjecting an adhesive site-containing monomer to copolymerization, (2) the method comprising carrying out the polymerization in an aqueous medium in the manner of emulsion polymerization, for instance, in the presence of an adhesive site-containing polymerization initiator to thereby introduce the polymerization initiator-derived adhesive site at one or each polymer chain terminus, and (3) the method comprising heating, for instance, the polymer on the occasion of polymerization or after polymerization to convert carbon-carbon single bonds in the polymer chain to double bonds to thereby provide the polymer with adhesive sites.

The method (1) mentioned above can be carried out, for example, by copolymerizing an adhesive site-containing monomer with fluorinated monomer species and composition selected according to the desired adhesive fluororesin, if desired together with a nonfluorinated monomer in the conventional manner known in the art.

The method of the above copolymerization is not particularly restricted but may comprise, for example, random copolymerization, which is carried out by introducing the adhesive site-containing monomer into the system on the occasion of polymer chain formation by other comonomers such as the fluorinated monomers, block copolymerization, or graft copolymerization. In the case of graft copolymerization, there may be mentioned, for example, the method comprising causing addition of an unsaturated carboxylic acid, which is to be mentioned later herein, to the fluoropolymer.

The "adhesive site-containing monomer" mentioned above means an adhesive site-containing polymerizable monomer which may contain one or more fluorine atoms or no fluorine atoms. In the present specification, the "fluorinated monomers" and "nonfluorinated monomers" mentioned above have no such adhesive site as mentioned above.

When the adhesive site is a carbonyl group-containing group or bond, the adhesive site-containing monomer includes, among others, fluorine-containing monomers such as perfluoroacrylic acid fluoride, 1-fluoroacrylic acid fluoride, acrylic acid fluoride, 1-trifluoromethacrylic acid fluoride and perfluorobutenoic acid; and fluorine-free monomers such as acrylic acid, methacrylic acid, acrylic acid chloride and vinylene carbonate.

As the adhesive site-containing monomer, there may further be mentioned unsaturated carboxylic acids.

The unsaturated carboxylic acid, so referred to herein, any compound containing at least one carbon-carbon unsaturated bond (hereinafter also referred to as "copolymerizable carbon-carbon unsaturated bond") enabling copolymerization and containing at least one carbonyloxy group [—C(=O)—O—], and those containing one copolymerizable carbon-carbon unsaturated bond in each molecule are preferred among others.

As the unsaturated carboxylic acids, there may be mentioned, for example, aliphatic unsaturated carboxylic acids and the corresponding acid anhydrides. The aliphatic unsaturated carboxylic acids may be aliphatic unsaturated monocarboxylic acids or aliphatic unsaturated polycarboxylic acids containing two or more carboxyl groups.

As the aliphatic unsaturated monocarboxylic acids, there may be mentioned, for example, aliphatic monocarboxylic acids containing 3 to 20 carbon atoms such as propionic acid, acrylic acid, methacrylic acid, crotonic acid, and anhydrides thereof. As the aliphatic unsaturated polycarboxylic acids, there may be mentioned maleic acid, fumaric acid, mesaconic acid, citraconic acid [CAC], itaconic acid, aconitic acid, itaconic acid anhydride [IAH] and citraconic acid anhydride [CAH].

As the polymerization initiator in the method (2) mentioned above, there may be mentioned diisopropyl peroxycarbonate, di-n-propyl peroxydicarbonate, tert-butylperoxy isopropyl carbonate, bis (4-tert-butylcyclohexyl) peroxydicarbonate and di-2-ethylhexyl peroxydicarbonate, among others.

The above-mentioned adhesive fluororesin preferably has a melting point of not higher than 200° C., more preferably not higher than 180° C. from the viewpoint of the sealability of the laminated film obtained.

In the present specification, the above-mentioned melting point is the temperature at the melting peak maximum value obtained by a measurement at a programming rate of 10° C./minute using a differential scanning colorimeter (product of Seiko).

In the practice of the invention, the adhesive fluoropolymer film may further have the form of a laminated film with a film other than the adhesive fluoropolymer film. In the practice of the invention, the laminated film may be any one resulting from lamination of at least the adhesive fluoropolymer film and a film other than the adhesive fluoropolymer film, with the adhesive fluoropolymer film forming the outermost layer of at least one side. The number of layers may be 2 or more. From the viewpoint of conduction of heat to the contents, that number is, but is not limited to, 2 to 5, preferably 2 or 3.

The thickness of the laminated film depends on the number of layers. In the case of a two-layer film consisting of a film other than the adhesive fluoropolymer film and the adhesive fluoropolymer film disposed on one side of the other film, the total film thickness is, but is not limited to, about 20 to 200 μm, preferably 20 to 100 μm, particularly preferably 20 to 60 μm, from the viewpoint of conduction of heat to the contents.

The thickness of the adhesive fluororesin layer mentioned above is preferably 5 to 100 μm, more preferably not thinner than 10 μm and not thicker than 50 μm.

In the practice of the invention, the laminated film, when formed by the above-mentioned thermal lamination method, generally can have a bond strength (x) of not lower than 200 N/m, preferably not lower than 300 N/m, more preferably not lower than 400 N/m.

In the present specification, the above-mentioned bohd strength (x) is the strength required for 180-degree peeling on a Tensilon universal testing machine at a speed of 25 mm/minute using 10-mm-wide specimens excised from the laminated film and provided with margins for gripping at one end by peeling the adhesive fluororesin layer from the film other than the adhesive fluororesin film such as a PI film using a cutter.

The film other than the adhesive fluororesin film is not particularly restricted provided that it is not a film made of the adhesive fluoropolymer; a low-temperature resistant resin is preferred, however.

The low-temperature resistant resin is a resin excellent in shock resistance at temperatures not higher than about −40° C., preferably at about −80° C. and lower temperatures. For example, mention may be made of ultrahigh molecular weight polyethylene, polyimides, polytetrafluoroethylene, ethylene-tetrafluoroethylene copolymers and ethylene-vinyl acetate copolymers. From the viewpoint of conduction of heat to the contents and of low-temperature resistance, polyimides, polytetrafluoroethylene and ethylene-tetrafluoroethylene copolymers are preferred. More preferred are polyimides. From the moldability/processability viewpoint, the molecular weight of the low-temperature resistant resin expressed in terms of number average molecular weight is, but is not limited to, about 1,000 to 1,000,000, preferably about 2,000 to 500,000, more preferably about 5,000 to 300,000.

The shock resistance mentioned above is evaluated by the impact test based on the free fall dart method (staircase method (JIS K 7124-1)) using the resin film or resin sheet just after taking out of a cryopreservation environment. Preferred as the resin excellent in shock resistance are those showing a 50% fracture energy (E50) of not lower than 0.1, preferably not lower than 0.2, more preferably not lower than 1.0, in the above-mentioned staircase method (at the temperature of liquid nitrogen).

The polyimide mentioned above may be any one comprising a heat-resistant polymer having imide bonds in the main chain thereof; it includes, but is not limited to, nonthermoplastic polyimides having imide bonds alone in the main chain, wholly aromatic polyimides, organic solvent-soluble polyimides, polyetherimides and polyimideamides, among others.

The above-mentioned low-temperature resistant resin film includes, but is not limited to, those formed of a low-temperature resistant resin by hot melting under high temperature and high pressure conditions, extrusion or compression, or solvent casting.

As the method of lamination of the adhesive fluoropolymer film and the film other than the adhesive fluoropolymer film to give the laminated film mentioned above, there may be mentioned the hot lamination method, hot compression method, high-frequency heating method and solvent casting method, among others. A preferred method is, but is not limited to, the hot lamination method from the ease of production viewpoint. The adhesive fluoropolymer film is firmly bonded to the film other than the adhesive fluoropolymer film, so that the adhesive fluoropolymer film will not peel off from the film other than the adhesive fluoropolymer film. From the safety production viewpoint, among others, the temperature conditions in the above-mentioned hot lamination method are, but are not limited to, about 200 to 300° C., preferably about 200 to 250° C.

In the practice of the invention, the laminated film can be formed by laminating the film other than the adhesive fluoropolymer film, for example the above-mentioned PI film, and the adhesive fluororesin.

The lamination of the PI film or a like film other than the adhesive fluoropolymer film and the adhesive fluororesin can be carried out by the extrusion lamination method, for instance, and can also be carried out by laminating the film other than the adhesive fluoropolymer film, for example a PI film, and the adhesive fluororesin by thermocompression bonding, for instance.

The above-mentioned extrusion lamination may comprise, for example, an extrusion step (a) in which the adhesive fluororesin is melted and extruded onto the above-mentioned PI film or alike film other than the adhesive fluoropolymer film, the compression bonding step (b) in which the PI film or a like film other than the adhesive fluoropolymer film and the adhesive fluororesin extruded are inserted between rolls for compression bonding and the take-up step (c) in which the laminate produced is taken up. Generally, the extrusion step (a), compression bonding step (b) and take-up step (c) are carried out in that order.

The preferred extrusion temperature range in the above extrusion step (a) varies according to the kind of the PI film or a like film other than the adhesive fluoropolymer film and the kind of the adhesive fluororesin, the desired laminated film thickness and other factors. Generally, the range is preferably not lower than the melting point of the adhesive fluororesin used but lower than the decomposition temperature of the same since laminated films high in interlaminar bond strength are obtained in that range.

In the above extrusion step (a), the rate of extrusion of the molten adhesive fluororesin onto the PI film or a like film other than the adhesive fluoropolymer film can be properly selected according to the adhesive fluororesin used and the composition and thickness, among others, of the PI film or a like film other than the adhesive fluoropolymer film. However, the step can be carried out within the range of 0.1 to 100 m/minute, for instance.

The above extrusion lamination, in particular the extrusion step (a), is preferably carried out in an inert gas and/or the PI film or a like film other than the adhesive fluoropolymer film is dried beforehand or deprived of moisture by preheating so that the laminated film high in interlaminar bond strength may be obtained.

In the practice of the invention, the extrusion lamination is considered to be characterized in that the adhesiveness of the adhesive sites occurring in the adhesive fluororesin is displayed in the extrusion step. When the extrusion lamination is carried out in an inert gas and/or the PI film or a like film other than the adhesive fluoropolymer film is dried in advance or deprived of moisture by preheating, supposedly, the adhesiveness can be fully displayed.

The operating conditions in the steps other than the extrusion step (a) in the above extrusion lamination can be properly selected in the conventional manner according to the kinds of the PI film or a like film other than the adhesive fluoropolymer film and the adhesive fluororesin, the intended thickness of the laminated film and other factors.

When the lamination of the PI film or a like film other than the adhesive fluorine-containing film and the adhesive fluororesin is to be carried out in the manner of thermocompression, the lamination can be carried out generally by molding the adhesive fluororesin into a film by the extrusion molding method known in the art, for instance, and laying the adhesive fluororesin film obtained and the PI film or a like film other than the adhesive fluoropolymer film one on the other and compressing the assembly with heating.

The above-mentioned thermocompression is preferably carried out at a temperature of 120 to 300° C. A more preferred lower limit to that temperature is 140° C., and a more preferred upper limit thereto is 280° C.

The PI film or a like film other than the adhesive fluoropolymer film may be preheated in advance or dried beforehand prior to the lamination by thermocompression bonding, for instance.

When the respective layers are laminated by thermocompression, for instance, the layers after lamination may be heated for aging so that the interlaminar bonding may be improved.

The heating for such aging is preferably carried out at 200 to 280° C.

The above-mentioned laminated film is shaped into a container or bag-like article by heat sealing. More specifically, two laminated films are placed one on the other so that the adhesive fluoropolymer films come into contact with each other and, then, heat sealing is carried out. The capacity of the package is, but is not limited to, about 5 to 500 ml, preferably about 10 to 300 ml, since the cryopreservation container generally has a capacity of about 2 to 200 ml. In view of the seal strength between the laminated films, the heat seal width is, but is not limited to, about 2 to 20 mm, preferably about 5 to 15 mm. Also from the viewpoint of the seal strength between the laminated films, the heat seal temperature is about 180 to 250° C., preferably about 200 to 220° C., General-purpose fluororesin films cannot be sealed at such low temperatures as 180 to 250° C. Thus, the adhesive fluoropolymer film according to the invention shows good sealability at low temperatures and therefore is low in production process cost.

The package for a cryopreservation container according to the invention is used for further packaging a cryopreservation container containing such a biological sample as erythrocytes, platelets, plasma or a like blood component, bone marrow fluid, another body fluid or a cell suspension. On that occasion, the air between the cryopreservation container and the package can favorably be removed with ease by the packaging method using an auxiliary device disclosed in Japanese Kokai Publication 2000-185716, for instance. The packaging method is not limited thereto, however.

The package for a cryopreservation container according to the invention can be produced by shaping the laminated films into a container or bag-like article by the heat seal technique, for instance. When laminated films having the outermost layer made of an adhesive fluoropolymer film at least one side are used as the above-mentioned laminated films, the package for a cryopreservation container as obtained can be a container having the adhesive fluoropolymer film as the outermost layer on at least one side thereof, preferably a container having the adhesive fluoropolymer film as the outermost layer on at least the inner side of the container.

The package for a cryopreservation container according to the invention can satisfactorily endure such very low temperatures as −80 to −196° C. In actually preserving such a blood component as erythrocytes, platelets or plasma, bone marrow fluid or another body fluid or a cell suspension, gradual cooling is preferred so that such tissues may not be damaged.

For example, there may be mentioned the method comprising once cooling the whole package to about −80° C. in a deep freezer (refrigerator), for instance, then transferring the same into liquid nitrogen for preservation. The method of storage is not limited to such method, however. On the occasion of using the stored blood or cells, for instance, the blood or cells can be thawed using means for warming, such as a warm bath at 37 to 40° C. The method of thawing is not limited to such, however.

In storing a biological sample in the above-mentioned cryopreservation container, a commercially available preserving fluid can be adequately used. In the case of storing cells, DMEM medium, RPMY 1640 medium, 199 medium and phosphate buffer may be mentioned as preserving fluids therefor. Preferably, about 0.5 to 2% by volume of albumin may be added. More preferably, dimethyl sulfoxide (DMSO) may be added as an agent for protecting against freeze damage at a final concentration of about 5 to 20% by volume. In the case of storing an organ, Euro-Collin's solution and UW solution, among others, may be mentioned. Preferably, dimethyl sulfoxide (DMSO) may be added as an agent for protecting against freeze damage at a final concentration of about 5 to 20% by volume. The selection and preparation of such a preserving fluid can be appropriately made by the one skilled in the art, hence are not particularly restricted.

As a method of freezing the package for a cryopreservation container according to the invention, there may be mentioned the method comprising freezing the package used for further packaging the cryopreservation container containing or storing a biological sample at 0° C. or below. Preferred as the method of freezing is the method comprising freezing at −80° C. or below. In the above method of freezing, the package is preferably cooled gradually to a desired temperature for freezing so that the biological sample may not be damaged. As such a method of freezing, there may be mentioned, for example, the method comprising cooling the package once to about −80° C. in a deep freezer (refrigerator) and the immersing the same in liquid nitrogen. The cryopreservation container may also contain such a preserving fluid as mentioned above according to need. The package is then generally freeze-preserved following freezing by the above method.

The package of the invention, which has the constitution described hereinabove, will not be broken even at such a very low temperature as the liquid nitrogen temperature (−196° C.) and will not show any decrease in sealability at the sealed portion. Therefore, it will never allow such a refrigerant as liquid nitrogen to enter the same and can prevent the contents from being contaminated or leaking out; thus, it shows good protective performance characteristics.

Furthermore, the above-mentioned package is tolerable in a low temperature range not so low as the above-mentioned very low temperatures provided that the temperature is lower than the melting point of the adhesive fluororesin used and can show resistance to a very wide temperature range and will never undergo breakage or show decreases in sealability at the sealed portion even upon rapid changes in temperature, for example when it is placed under ordinary temperature conditions after placement at the above-mentioned very low temperatures.

While the mechanisms why the package of the invention produces such excellent effects as mentioned above are not clear, the following characteristics presumably produce synergistic effects: (1) the PI is resistant to very low temperatures and can maintain the shape of the molded article even at very low temperatures as the liquid nitrogen temperature, (2) the package is excellent in the interlaminar adhesion between the PI film and the adhesive fluororesin layer, (3) the PI film and the adhesive fluororesin layer can be bonded directly without using any adhesive agent and, therefore, the problems encountered in using an adhesive agent, namely the problem of embrittlement and breakage of the adhesive layer at such very low temperatures as the liquid nitrogen temperature and the problem of outgas emission and substance elution from the adhesive layer, can be avoided and (4) the package is formed from the laminated films obtained by lamination of the PI film and the adhesive fluororesin layer by mutual thermowelding of the adhesive fluororesin layers and therefore is excellent in the mutual adhesion between the adhesive fluororesin layers and has reliable sealability.

The package for a cryopreservation container according to the invention can be suitably used in packaging a cryopreservation container.

The cryopreservation container can be suitably used as a cryopreservation container for a biological sample. As the biological sample that can be stored in the above cryopreservation container, there may be mentioned, for example, human-derived biological samples, biological samples derived from animals other than humans or from plants, viruses, microorganisms and like biological samples.

The above cryopreservation container is a container capable of containing, in a tightly closed condition, such a biological sample as a blood component, cells, a tissue, an organ, viruses, bacteria, sperms, ova or fertilized ova, for instance. For example, mention may be made of commercially available polypropylene vials and the containers disclosed in Patent Documents 1 to 4. Preferred ones from the low-temperature resistance viewpoint are, but are not limited to, freezing bags for medical use which are disclosed in Patent Document 4 and constituted of laminated films consisting of an ultrahigh molecular weight polyethylene film and a thermoplastic resin film compatible with the ultrahigh molecular weight polyethylene.

As the blood component, there may be mentioned whole blood, erythrocytes, leukocytes, plasma, platelets and platelet rich plasma, among others. As the cells, there may be mentioned rare cells such as hematopoietic stem cells, ES cells, mesenchymal stem cells, mononuclear marrow cells, spermatids and egg cells as well as common cells such as neurocytes, epithelial cells and fibroblasts. Further, as the vital tissues, there may be mentioned various tissues and organs such as tendons, nerves, ligaments, esophagi, tracheas, Langerhans islands, mucoepithelial tissues, keratoepithelial tissues, cultured corneal tissues and like membranous tissues as well as organs such as pancreases, hearts, lungs, livers and kidneys. As the viruses, there may be mentioned hepatitis B virus, hepatitis C virus, coronavirus and mosaic virus, among others. As the bacteria, there may be mentioned *Mycobacterium tuberculosis, Haemophilus influenzae, Escherichia coli, Staphylococcus aureus, hemolytic streptococci* and *Klebsiella pneumoniae*, among others. Further, sperms, ova and fertilized ova may be mentioned in relation to the field of infertility treatments, for instance. These blood or blood components, cells including rare cells and other vital tissues to be stored are selected at the workers' discretion according to the intended purpose, hence are not particularly restricted.

As the vital tissues, there may further be mentioned, for example, living organism-derived body fluids (blood, cerebrospinal fluid, lymph, etc.) and components thereof (erythrocytes, leukocytes, platelets, plasmas, sera, etc.), living organism-derived tissues (blood vessels, corneas, menisci, cerebral tissues, skins, subcutaneous tissues, epithelial tissues, osseous tissues, muscular tissues, etc.), organs (eyes, lungs, kidneys, hearts, livers, pancreases, spleens, digestive tracts, bladders, ovaries, testicles, etc.), various cells (hematopoietic stem cells such as cord blood- or peripheral blood-derived hematopoietic stem cells, marrow cells, hepatocytes, splenocytes, brain cells and other various organ cells, neurocytes, sperms, egg cells, fertilized ova, embryonic stem cells (ES cells), cancer cells for research and therapeutic purposes, cultured cells, stem cells, germ cells, etc.) and so forth.

As the biological samples, there may be mentioned human vital tissues, inheritance-related substances and, further, vital tissues and inheritance-related substances derived from animals including small animals such as small experimental animals; microorganisms, bacteria, and inheritance-related substances derived therefrom; and so forth. These are used in the research field, for instance.

As the biological samples, there may further be mentioned vital tissues and inheritance-related substances derived from domestic animals and animals and those used in the fields of researches, cultures, cultivations, horticulture and agriculture.

As the biological samples, there may also be mentioned plant seeds, pollens, cultured cells, shoot apex cells and inheritance-related substances.

As the biological samples, there may further be mentioned vital tissues and inheritance-related substances derived from marine algae, fish and the like. These are used, for example, in researches in the field of fishery sciences.

As the inheritance-related substances, there may be mentioned DNAs, hosts, vectors and so forth.

The biological samples mentioned above can be used for medical purposes; in research and development in the fields of agriculture, animal husbandry, forestry, fishery, horticulture and so forth; in the treatment of diseases, infertility treatment and breeding of animals in the pet industry and animal industry and for the cloning technology, for instance.

Thus, the cryopreservation container mentioned above can be used in various fields such as medical treatment; researches; animal husbandry, horticulture and agriculture; and fishery, and the package for such cryopreservation container according to the invention can also be used in various fields.

EXAMPLES

The following examples illustrate the present invention in detail. These examples are, however, by no means limitative of the scope of the invention.

Examples 1 to 4

Production of Packages for Cryopreservation Containers

A two- or three-layer film was produced by the hot lamination method using a polyimide film and one or two films made of a ternary system random copolymer produced from tetrafluoroethylene, perfluoro (vinyl propyl ether) and perfluoro (1,1,9,9-tetrahydro-2,5-bistrifluoromethyl-3,6-dioxa-8-nonenol) (hereinafter referred to as "inner layer fluororesin film" and "outer layer fluororesin film") as applied to one side or both sides of the polyimide film. Sheets with a size of 100×95 mm were cut from each film and packages (25 ml in capacity) for cryopreservation containers were produced by laying one of two sheets on top of the other so that the inner layer fluororesin films came into contact with each other and heat-sealing 2-mm-wide margins. The polyimide film thickness and inner layer fluororesin film thickness data are shown in Table 1.

The copolymer composition of the ternary system random copolymer film was such that the ratio of perfluoro(1,1,9,9-tetrahydro-2,5-bistrifluoromethyl-3,6-dioxa-8-nonenol) monomer units to tetrafluoroethylene monomer units plus perfluoro (vinyl propyl ether) monomer units was 1:99. The copolymer composition was determined by $^{19}$F-NMR.

Comparative Example 1

Packages made of a perfluoroethylene-propylene copolymer were used as packages for cryopreservation containers for comparison.

Reference Example 1

Cryopreservation Containers to be Packaged in Packages

Cryopreservation containers made of a laminated film produced by laminating an ultrahigh-molecular-weight polyethylene film and two low-molecular-weight polyethylene films on both sides of the former were used.

Synthesis Example 1

Synthesis of an Adhesive Fluororesin

A 820-liter glass-lined autoclave was charged with 200 L of pure water, the system inside was thoroughly purged with nitrogen gas and then the nitrogen was evacuated therefrom. The autoclave was charged with 113 kg of 1-fluoro-1,1-dichloroethane, 95 kg of hexafluoropropylene and 85 g of cyclohexane. Then, 292 g of perfluoro (1,1,5-trihydro-1-pentene) [$CH_2=CF(CF_2)_3H$] was fed to the autoclave under pressure using nitrogen gas, and the vessel inside temperature was maintained at 35° C. and the rate of stirring at 200 rpm. Further, tetrafluoroethylene was fed to the autoclave until arrival of the pressure at 7.25 kg/cm$^2$G, followed by feeding of ethylene until arrival of the pressure at 8 kg/cm$^2$G.

Then, the polymerization was started by feeding 1.9 kg of a 50% (by mass) solution of di-n-propyl peroxydicarbonate in methanol. Since otherwise the vessel inside pressure fell with the progress of the polymerization, a tetrafluoroethylene/ethylene/hexafluoropropylene mixed gas (mole ratio=39.2:43.6:17.3) was additionally fed under pressure and, while maintaining the polymerization pressure at 8 kg/cm$^2$G in that manner, the polymerization was continued and, during the polymerization, 1100 g of $CH_2=CF(CF_2)_3H$, divided in 20 portions, was charged using a micropump. The polymerization was carried out for a total of 32 hours. After completion of the polymerization, the contents were recovered and washed with water to give 95 kg of a powdery adhesive fluororesin.

The adhesive fluororesin obtained was subjected to the following measurements.

(1) Monomer Units $^{19}$F-NMR analysis was carried out and determinations were made.

(2) Number of Carbonate Groups

A film with a thickness of 0.05 to 0.2 mm was prepared by compression molding of the adhesive fluororesin powder at room temperature. The film obtained was subjected to infrared absorption spectrometry, and the absorbance of the peak [1809 cm$^{-1}$ ($v_{c=o}$)] assignable to the carbonyl group in the carbonate group [—OC(=O)—O—] was measured. The number of carbonate groups per 1×10$^6$ main chain carbon atoms was calculated based on the measured value obtained according to the formula given below.

N=500AW/εdf

A: Absorbance at the above-mentioned $v_{c=o}$

ε: Molar extinction coefficient at the above $v_{c=o}$ [1·cm$^{-1}$·mol$^{-1}$]

(The value ε=170 was employed based on the results with model compounds.)

W: Composition average molecular weight calculated based on the monomer composition d: Film density [g/cm$^3$]

f: Film thickness [mm] measured using a micrometer.

The above infrared absorption spectrometry was carried out by making 40 scans on Perkin-Elmer FTIR spectrometer 1760X (product of Perkin-Elmer). The analysis of the absorbance of $v_{c=o}$ was carried out using Perkin-Elmer Spectrum for Windows (registered trademark) Ver. 1.4C software.

(3) Melting Point

The measurement was carried out at a programming rate of 10° C./minute using a differential scanning calorimeter (product of Seiko) and the temperature at the maximum of the melting peak obtained was regarded as the melting point.

The adhesive fluororesin obtained had a monomer unit composition of TFE/Et/HFP/$CH_2=CF(CF_2)_3H$=38.9/45.9/14.8/0.4, the number of carbonate groups was 411 per 1×10$^6$ main chain carbon atoms and the melting point thereof was 171.8° C.

Example 5

(1) The adhesive fluororesin obtained in the synthesis example was molded into an adhesive fluororesin film (thickness: 25 μm) through a T die mounted on a single screw extruder with a cylinder diameter of 90 mm under the conditions of a cylinder temperature of 170 to 230° C., a die temperature of 230° C. and a screw speed of 10 rpm. The adhesive fluororesin film obtained and a polyimide film (product name: Kapton 100H, product of Du Pont Toray, thickness: 25 μm) were laminated using a hot roll at a temperature of 250° C. to give a laminated film (length 20 m×width 200 mm×total thickness 50 μm; hereinafter referred to also as "continuous film"). Rectangular specimens, 100 mm in the lengthwise direction and 10 mm in the transverse direction, were cut out from the laminated film obtained (fluororesin layer thickness: 25 μm, polyimide layer thickness: 25 μm). Each specimen was provided with margins for gripping at one end by peeling the adhesive fluororesin layer from the polyimide layer using a cutter and subjected to 180-degree peeling on a Tensilon universal testing machine (product of Orientec) at a speed of 25 mm/minute. The bond strength of the laminated film was 400 N/m.

(2) Then, two 12-cm-square laminated film sheets were excised from the above-mentioned continuous sheet and placed one on top of the other with the adhesive fluororesin layers inside, and three sides were fusion-bonded by heating at 210° C. for 5 seconds using a heat sealer. The seal width (bonding part width) was 1 cm. Thus, a package (capacity: 25 ml) for a cryopreservation container was formed. The thickness of the polyimide film and the thickness of the adhesive fluororesin film (inner layer fluororesin film) are shown in Table 1.

TABLE 1

|  | Inner layer fluororesin film | Polyimide film |
| --- | --- | --- |
| Example 1 | 25 μm | 25 μm |
| Example 2 | 50 μm | 25 μm |
| Example 3 | 25 μm | 50 μm |
| Example 4 | 50 μm | 50 μm |
| Example 5 | 25 μm | 25 μm |

Experimental Example 1

Freezing Test

A 10% (by volume) aqueous solution of DMSO (in about 25-ml portions) was packed in cryopreservation containers described in Reference Example 1. These cryopreservation containers were packaged with the packages of Examples 1 to 5 and Comparative Example 1, respectively, and were put in aluminum cases, respectively. The cases were allowed to stand in a deep freezer (refrigerator) at −80° C. for 4 hours for freezing the contents. After this freezing treatment, the packages with the respective cryopreservation containers in the aluminum cases were transferred into liquid nitrogen and stored for 1 week.

The stored packages with the respective cryopreservation containers were taken out of the aluminum cases and placed in a warm bath at 37 to 40° C. for thawing, and each package was observed by the eye as to whether there was any damage or liquid nitrogen intrusion or some other trouble.

The results of this experiment are shown in Table 2. In Comparative Example 1, the percent breakage was 2%, whereas the packages for cryopreservation containers according to the invention all showed no breakage at all in spite of the great number of tests, namely 100 packages in each example.

TABLE 2

|  | Number of damaged packages/ number of packages tested |
| --- | --- |
| Example 1 | 0/100 |
| Example 2 | 0/100 |
| Example 3 | 0/100 |
| Example 4 | 0/100 |

TABLE 2-continued

|  | Number of damaged packages/ number of packages tested |
| --- | --- |
| Example 5 | 0/100 |
| Comparative Example 1 | 2/100 |

Experimental Example 2

Freezing Test

A cell suspension was prepared by suspending MOLT-4 cells (obtained from RIKEN) in RPMI 1640 medium (product of Invitrogen) to a concentration of about $1.0 \times 10^7$ cells/ml. This cell suspension was packed, in about 25-ml portions, in cryopreservation containers described in Reference Example 1. These cryopreservation containers were packaged with the packages of Example 5 and Comparative Example 1, respectively, and were put in aluminum cases, respectively. The cases were allowed to stand in a deep freezer (refrigerator) at −80° C. for 4 hours for freezing the contents. After this freezing treatment, the packages with the respective cryopreservation containers in the aluminum cases were transferred into liquid nitrogen and stored for 1 week. The stored packages with the respective cryopreservation containers were taken out of the aluminum cases and placed in a warm bath at 37 to 40° C. for thawing, and each package was observed by the eye as to whether there was any damage or liquid nitrogen intrusion or some other trouble. In each example, 10 tests were performed.

As a result, one cryopreservation container package was found damaged in Comparative Example 1 whereas the 10 cryopreservation container packages according to the invention showed no damage at all.

INDUSTRIAL APPLICABILITY

The package for a cryopreservation container according to the invention makes it possible to store blood, rare cells and vital tissues in a very low temperature environment without any damage to the package/container. Since it has a relatively thin film thickness, it will not reduce the conduction of heat to the contents of the cryopreservation container in the package. Further, the sealing strength resulting from heat sealing after placing a cryopreservation container in the packages is very good and, therefore, liquid nitrogen can be inhibited from entering the inside and thus contamination with bacteria, viruses or the like contained in liquid nitrogen can be avoided and the package can be prevented from being broken by expansion of intruder liquid nitrogen on the occasion of thawing.

The invention claimed is:

1. A method for packaging a cryopreservation container, which comprises producing a package by shaping a laminated film comprising at least an adhesive fluoropolymer film on at least one outermost layer and a film other than said adhesive fluoropolymer film, into a bag-like article by heat sealing at 180-250° C., packaging the cryopreservation container in the package, wherein the adhesive fluoropolymer film is made of an adhesive fluoropolymer containing at least one adhesive site, wherein the at least one adhesive site is selected from the group consisting of carbon-carbon double bond, carbonyl group [—C($=$O)], carbonyl group-containing groups or bonds, hydroxyl group, cyano group, sulfonic acid group and epoxy group,
wherein the film other than the adhesive fluoropolymer film is a low-temperature resistant resin film,
wherein the low-temperature resistant resin comprises at least one resin selected from the group consisting of ultrahigh molecular weight polyethylene, polyimides, polytetrafluoroethylene, ethylene-tetrafluoroethylene copolymers and ethylene-vinyl acetate copolymers.

2. The method according to claim 1,
wherein the adhesive fluoropolymer contains at least one reactive functional group as the adhesive site and is a copolymer obtained by copolymerizing the following monomers (A) and (B):
(A) A fluorinated monomer containing no reactive functional group;
(B) A fluorinated monomer containing the at least one reactive functional group.

3. The method according to claim 2,
wherein the fluorinated monomer containing no reactive functional group is represented by the formula (1) given below:

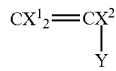

(wherein $X^1$ and $X^2$ each is hydrogen atom or halogen atom and Y is hydrogen atom, fluorine atom, a fluorinated alkyl group containing 1 to 5 carbon atoms or a fluorinated oxyalkyl group containing 1 to 5 carbon atoms, and wherein, the monomer of (1) contains at least one fluorine atom).

4. The method according to claim 3,
wherein the fluorinated monomer containing no reactive functional group comprises at least one monomer selected from the group consisting of tetrafluoroethylene, vinylidene fluoride, 1,2-difluorochloroethylene, hexafluoropropylene, perfluoro(vinyl methyl ether) and perfluoro(vinyl propyl ether).

5. The method according to claim 2,
wherein the fluorinated monomer containing the at least one reactive functional group is represented by the formula (2) given below:

(wherein $X^1$ and $X^2$ each is hydrogen atom or halogen atom, Z is hydroxyl group, carboxyl group, cyano group, sulfonic acid group or epoxy group and $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond).

6. The method according to claim 1,
wherein the adhesive fluoropolymer is represented by the formula (3) given below:

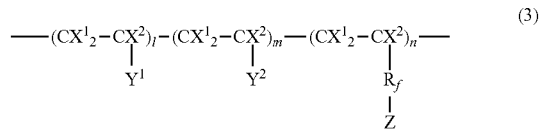

(wherein $X^1$ and $X^2$ each is hydrogen atom or halogen atom, $Y^1$ and $Y^2$ each is hydrogen atom, fluorine atom, a fluorinated alkyl group containing 1 to 5 carbon atoms or a fluorinated alkoxy group containing 1 to 5 carbon atoms, Z is hydroxyl group, carboxyl group, cyano group, sulfonic acid group or epoxy group, $R_f$ is a fluorinated alkylene group containing 1 to 40 carbon atoms, a fluorinated oxyalkylene group containing 1 to 40 carbon atoms or a fluorinated alkylene group containing 1 to 40 carbon atoms and at least one ether bond and the ratio $(l+m)/n$ is 2 to 2000).

7. The method according to claim 1,
wherein the adhesive fluoropolymer comprises a fluorinated monomer-derived fluorinated monomer unit and a nonfluorinated monomer-derived nonfluorinated monomer unit.

8. The method according to claim 7,
wherein the fluorinated monomer is tetrafluoroethylene and the nonfluorinated monomer is ethylene.

9. The method according to claim 1,
wherein the low-temperature resistant resin is a polyimide.

* * * * *